United States Patent
Souvie et al.

(10) Patent No.: US 7,425,529 B1
(45) Date of Patent: Sep. 16, 2008

(54) NON-ETHANOL PERFUME COMPOSITIONS COMPRISING HYDROFLUOROETHER

(75) Inventors: Marie-Laure Souvie, Orléans (FR); Gérard Baton, Chartres (FR)

(73) Assignee: LVMH Recherche, Paris (FR)

(*) Notice: Subject to any disclaimer, the term of this patent is extended or adjusted under 35 U.S.C. 154(b) by 1224 days.

(21) Appl. No.: 10/069,103

(22) PCT Filed: Aug. 25, 2000

(86) PCT No.: PCT/FR00/02384

§ 371 (c)(1),
(2), (4) Date: Feb. 22, 2002

(87) PCT Pub. No.: WO01/13875

PCT Pub. Date: Mar. 1, 2001

(30) Foreign Application Priority Data

Aug. 26, 1999 (FR) .................. 99 10821

(51) Int. Cl.
*A61Q 13/00* (2006.01)

(52) U.S. Cl. ............................. 512/2; 512/1

(58) Field of Classification Search ............ 512/1; 252/364
See application file for complete search history.

(56) References Cited

U.S. PATENT DOCUMENTS

| | | | | |
|---|---|---|---|---|
| 4,110,626 A | * | 8/1978 | Katada et al. ............... | 512/2 |
| 5,234,689 A | * | 8/1993 | Lindauer et al. ........... | 424/401 |
| 6,228,282 B1 | * | 5/2001 | Shimomura et al. ........ | 252/68 |
| 6,573,235 B1 | * | 6/2003 | Surbled et al. ............. | 512/1 |

FOREIGN PATENT DOCUMENTS

| | | |
|---|---|---|
| EP | 0845523 | 6/1998 |
| EP | 1029527 | 8/2000 |
| JP | 04159399 A * | 6/1992 |
| WO | WO 94/10970 | 5/1994 |
| WO | WO 9926600 A1 * | 6/1999 |

OTHER PUBLICATIONS

Komata et al. JP 04159399 A, Jun. 1992, Translation.*

* cited by examiner

*Primary Examiner*—Yelena G. Gakh
(74) *Attorney, Agent, or Firm*—Clark & Brody

(57) ABSTRACT

The invention relates to an ethanol-free or alcohol-free composition.

This ethanol-free or alcohol-free composition comprises a hydrofluoro ether and is characterized in that it comprises at least one ester of a polyacid, preferably a hydroxylated polyacid.

This composition can be used in the preparation of perfume compositions such as perfumes and toilet waters.

30 Claims, No Drawings

NON-ETHANOL PERFUME COMPOSITIONS COMPRISING HYDROFLUOROETHER

The invention relates essentially to a non-ethanolic composition comprising a perfluorinated hydrofluoro ether and at least one co-solvent, other than water and ethanol, comprising a polyacid ester, and to its use in perfume compositions.

Such perfume compositions are preferably ethanol-free perfume compositions of which all the components are miscible with one another to give the composition the appearance of a clear liquid.

In perfume products (perfume, toilet water, etc.), the presence of alcohol (ethanol), which is used mainly as a solubilizer for the perfume concentrate, presents a number of problems well known to those skilled in the art. It is for this reason that research has been carried out for many years on perfume products which avoid the addition of alcohol by replacing it with other solubilizers.

As examples, reference may be made to the documents WO 99/18925 and U.S. Pat. No. 5,468,725, which describe alcohol-free perfume compositions and respectively use silicones as solubilizer and the microemulsion technique.

One of the general problems which arise is the olfactory preservation of the perfume concentrate composition and especially the olfactory neutrality of the solubilizers used.

Furthermore, the document WO 99/11225 discloses cosmetic preparations in which the essential ingredients are at least 1% of hydrofluoro ether for the purpose of improving the tolerability of these compositions on the skin and improving the feel of the cosmetic product.

Also, the document WO 99/26600 discloses the use of perfiluorinated hydrofluoro ethers as agents for dissolving aromatic compounds in the preparation of a cosmetic composition. On page 3, lines 21 to 25, said document envisages in general terms the possibility of adding at least one co-solvent, which is indicated as preferably being selected from the group comprising ethanol and water, i.e. in practice an aqueous-alcoholic mixture. The Examples given in said document all relate to the exclusive use of a hydroperfluoro ether for solubilizing essential oils. The hydroperfluoro ethers mentioned are methoxynonafluorobutane, abbreviated to MNFB, in Examples 1 and 2, ethoxynonafluorobutane, abbreviated to ENFB, in Examples 3 to 8, and also propoxyundecafluoropentane.

A specific problem exists with perfume compositions, namely the necessary solubility of all the constituents of such a perfume composition. A principal component is made up of a perfume concentrate containing essential oils together with various components such as emulsifiers or surfactants, fatty esters or cellulose derivatives, together with other components well known to those skilled in the art.

In the context of experiments performed with a view to obtaining ethanol-free or alcohol-free compositions, the Applicant performed experiments aimed at verifying whether perfluorinated hydrofluoro ethers were capable on their own of totally solubilizing such perfume concentrates in order to prepare perfume compositions, these perfume concentrates being commercially available and marketed by companies specialized in their manufacture, such as GIVAUDAN, Switzerland, FIRMENICH, Switzerland, or International Flavors & Fragrances (IFF), USA. Now, all the experiments turned out negative in the sense that the liquids obtained were not clear but were obviously made up of two distinct phases.

One main object of the present invention is thus to solve the novel technical problem consisting in the provision of a solution which makes it possible to prepare compositions capable of achieving complete solubilization of perfume concentrates to give an essentially clear liquid, especially for the purpose of preparing perfume compositions.

Another main object of the present invention is to solve the novel technical problem consisting in the provision of a solution which makes it possible to effect the abovementioned solubilization of perfume concentrates with the aid of solubilizers which are neutral or substantially neutral towards the olfactory properties of said perfume concentrate, especially with a view to preparing perfume compositions of excellent quality.

Another main object of the present invention is to solve both the novel technical problems stated above by means of a solution which is free of ethanol or alcohol and which does not use water, ethanol or mixtures thereof as co-solvent.

The invention makes it possible for the first time to solve all these technical problems in a satisfactory and simple manner which can be used on the industrial and cosmetic scale, especially for the development of ethanol-free or alcohol-free perfume compositions of excellent quality, particularly perfumes and toilet waters.

Thus, according to a first feature, the present invention provides an ethanol-free or alcohol-free composition comprising a hydrofluoro ether, characterized in that it comprises at least one polyacid ester.

It has been discovered, surprisingly, that the combination of a hydrofluoro ether and a polyacid ester, acting as co-solvent, makes it possible to effect a virtually perfect or perfect solubilization of perfume concentrates to afford an essentially clear solution for the manufacture of perfume compositions of excellent quality. Moreover, it has been observed, also surprisingly, that the combination of the hydrofluoro ether and the polyacid ester forms a solubilizer which is neutral or essentially neutral from an olfactory point of view towards the perfumes in question.

The hydrofluoro ether component is preferably a perfluorinated component. These compounds are well known to those skilled in the art; they are for example of the type described in the document WO 99/11225 and can have the general formula $C_nH_mF_p$—O—$C_xH_yF_z$, in which n is a number ranging from 1 to 12, m is a number ranging from 0 to 25, p is a number ranging from 0 to 11, m+p=2n+1, x is a number from 1 to 12, y is a number from 0 to 25, x is a number from 0 to 11 and y+z=2x+1. In this formula, m and y may not be equal to 0 simultaneously and p and z may not be equal to 0 simultaneously, as described in said document to ensure the exactness of the chemical formula.

Some perfluorinated hydrofluoro ether compounds of the above general formula, namely methoxynonafluorobutane, ethoxynonafluorobutane and propoxyundecafluoropentane, are described in the document WO 99/26600. The commercially available methoxyheptafluoropropane can also be used.

The abovementioned polyacid ester is preferably an ester of a hydroxylated or non-hydroxylated polyacid and is also preferably formed with a saturated or unsaturated, linear or branched alcohol having between 1 and 30 carbon atoms, preferably between 1 and 12 carbon atoms, particularly ethanol, isopropanol or 2-ethylhexanol.

The polyacid preferably has between 3 and 10 carbon atoms. The carbon chain of the polyacid can be linear or branched and saturated or unsaturated with one or more units of unsaturation.

Furthermore, the carbon chain of the polyacids can be substituted by one or more hydroxyl groups or can contain one or more ketone groups. The abovementioned hydroxyl groups can be acetylated.

The polyacid esters which can be used to carry out the invention are preferably substantially non-polar.

They can be partial or total esters of the polyacid.

Preferably, all the acid groups of the polyacid are esterified.

Preferably, where groups with long carbon chains are involved, these chains are branched, as in the case of the 2-ethylhexyl group, which comprises 8 carbon atoms.

The preferred ester groups are the ethyl, isopropyl and 2-ethylhexyl groups.

The polyacids which can be used according to the invention are advantageously selected from:

→saturated diacids such as:
  malonic acid
  succinic acid
  glutaric acid
  adipic acid
  pimelic acid
  suberic acid
  azelaic acid →monounsaturated diacids such as:
  fumaric acid
  maleic acid
  citraconic acid*
  itaconic acid
  mesaconic acid
    *(branched diacid)

→diunsaturated diacids such as:
  muconic acid

→monohydroxylated diacids such as:
  tartronic acid
  malic acid
  citramalic acid →dihydroxylated diacids such as:
  dihydroxymaleic acid
  tartaric acid →tetrahydroxylated diacids such as:
  dihydroxytartaric acid
  galactaric acid
  glucaric acid →keto diacids such as:
  mesoxalic acid
  oxalacetic acid
  2-oxoglutaric acid
  3-oxoglutaric acid →diketo diacids such as:
  2,3-diketoadipic acid →saturated triacids such as:
  tricarballylic acid
  citric acid (monohydroxylated triacid)

→unsaturated triacids such as:
  aconitic acid

The preferred polyacids are citric acid and more particularly adipic acid.

The citric acid esters are preferably triethyl citrate, tri(2-ethylhexyl) citrate and acetyltriethyl citrate. These esters are commercially available.

The preferred adipic acid esters are diisopropyl adipate (often called isoadipate) and di(2-ethylhexyl) adipate. These esters are also commercially available.

The proportions by weight of the polyacid ester relative to the hydrofluoro ether component can vary within limits which do not substantially modify the olfactory character of the perfumes. In general, the polyacid ester may represent from 0.1 to 30% by weight, particularly from 1 to 20% by weight, of the hydrofluoro ether component.

Provision can also be made for any other complementary component in said composition, particularly a second co-solvent, such as a silicone, or a component for improving the properties of a perfume composition, such as the persistence of said composition on the skin, an example being a phthalate such as diethyl phthalate. However, silicone is preferred because it simultaneously combines the property of a co-solvent, or solubilizing additive, and the property of persistence.

Preferably, the proportion of silicone will be calculated so as to correspond to about 1 to 20% by weight, based on the weight of the final perfume composition.

Silicones which may be used are a dimethicone or a cyclomethicone, particularly the commercially available pentacyclomethicone, or an organotrisiloxane such as the one described in the PCT document published under the number WO 99/06018 and marketed in particular under the name SILATRIPHENE by RHODIA, France. Advantageously, it will be possible to use volatile silicones, particularly dimethicones marketed by the American company DOW CORNING, such as DC200 Fluid 1 centiStokes or, preferably, DC200 Fluid 0.65 centiStokes.

This composition can also comprise various additives normally used in the preparation of perfume or toilet water compositions, for example UV filters, antioxidants, antioxidants, colors, etc. Such complementary additives will generally be added in a proportion which can range up to 2% by weight of the final composition.

In a first preferred embodiment, the invention provides an ethanol-free or alcohol-free composition comprising a hydrofluoro ether, characterized in that it comprises the following in percentages by weight:
  hydrofluoro ether . . . 65 to 85%
  citric acid triester (such as triethyl citrate) . . . 4 to 7%
  2nd co-solvent or solubilizer: silicone such as DC200 Fluid from DOW CORNING, USA . . . 8 to 16%
  perfume concentrate . . . 5 to 20%

In a second preferred embodiment, the invention provides an ethanol-free or alcohol-free composition comprising a hydrofluoro ether, characterized in that it comprises the following in percentages by weight:
  hydrofluoro ether . . . 65 to 85%
  perfume concentrate . . . 0.5 to 20%
  iso-adipate (or diisopropyl adipate) . . . 10 to 20%

Within the framework of the invention, the hydrofluoro ether generally serves to make up the remainder of the composition, but the latter can optionally comprise the various additives normally used in the preparation of the abovementioned perfume or toilet water compositions.

It has been observed, within the framework of the invention, that compositions using iso-adipate as the 2nd co-solvent or solubilizing additive generally have a less greasy feel than compositions using the association or combination of citrate and silicone.

This represents an important technical advantage, unexpected for those skilled in the art, because the feel of compositions based on iso-adipate is thus closer to that of the conventional alcoholic perfume compositions such as toilet waters and perfumes.

According to a second feature, the present invention also covers the use of a polyacid ester, as defined above, in combination with a hydrofluoro ether as solubilizer for a perfume concentrate, especially with a view to preparing perfume compositions such as perfumes or toilet waters.

According to a third feature, the present invention also covers an ethanol-free or alcohol-free perfume composition comprising a perfume concentrate and a hydrofluoro ether, characterized in that it also comprises at least one polyacid ester in a sufficient amount to give said composition an essentially clear appearance.

This perfume composition will advantageously comprise from about 65 to about 85% by weight of hydrofluoro ether component, based on the final weight of the perfume composition.

According to another advantageous characteristic of this perfume composition, it will comprise from about 1 to about 20% by weight, preferably from 3 to 20% by weight, of abovementioned polyacid ester, based on the final weight of the perfume composition.

According to another advantageous characteristic of the perfume composition, it will comprise from about 5 to about 20% by weight of perfume concentrate. In this context, the concentration of perfume concentrate in the case of toilet water will generally be in the order of 5% by weight, based on the final weight of the toilet water. The concentration of perfume concentrate in the case of perfume will generally be between 10 and 20% by weight of the final perfume composition.

Thus the perfume composition will preferably consist of a toilet water or a perfume.

Of course, whether applying to the second feature or the third feature, various modified embodiments result from the first feature. Thus the hydrofluoro ether and the polyacid ester are as defined within the framework of the first feature. The same applies to any other complementary component which may be present and which has been described within the framework of the first feature.

Furthermore, within the framework of any one of the features of the invention, the composition can advantageously contain up to 2% by weight, based on the final composition, of any additive normally used in the preparation of perfume compositions such as perfumes or toilet waters, examples being UV filters, antioxidants, colors, etc.

The process for the preparation of the composition is easy to understand for those skilled in the art. The general procedure will be initially to add the polyacid ester to the perfume concentrate and then to add any complementary compounds, particularly a second co-solvent, such as a silicone, or a component for improving the properties of the perfume composition, such as the persistence of the composition on the skin, an example being a phthalate mentioned above, any other additives, particularly UV filters, antioxidants or colors, and finally the hydrofluoro ether component, which will preferably be added last and may also generally make up the remainder of the formulation.

The present invention will now be illustrated with the aid of Examples of ethanol-free or alcohol-free perfume and toilet water compositions with a totally clear appearance or the appearance of a perfect solution; said Examples are given simply by way of illustration and cannot therefore limit the scope of the invention in any way. Unless indicated otherwise, the percentages in the Examples are given by weight.

EXAMPLE 1

Of an Ethanol-Free or Alcohol-Free Perfume Composition According to the Invention This perfume composition has the following formulation:
ethoxynonafluorobutane . . . 68%
triethyl citrate . . . 8%
commercially available perfume concentrate . . . 20%
diethyl phthalate . . . 4%

This composition is prepared in the following manner:

The triethyl citrate is first added to the commercially available perfume concentrate and the two are intimately mixed; this is followed by addition of the diethyl phthalate and finally the ethoxynonafluorobutane.

The perfume composition prepared in this way, without ethanol or alcohol, is found to have a totally clear appearance or the appearance of a perfect solution, and the olfactory properties of the perfume concentrate are found to be totally preserved.

EXAMPLE 2

Of an Ethanol-Free or Alcohol-Free Perfume Composition According to the Invention This perfume composition has the following ingredients:
methoxynonafluorobutane . . . 71%
trioctyl citrate . . . 6%
silicone ref. DC200 Fluid 0.65 cs from DOW CORNING 8%
commercially available perfume concentrate . . . 15%

This composition is prepared in a similar manner to that of Example 1, the silicone being added after the citrate.

Again it is found that this composition has a totally clear appearance or the appearance of a perfect solution and that the olfactory properties of the perfumes are totally preserved.

EXAMPLE 3

Of an Ethanol-Free or Alcohol-Free Perfume Composition According to the Invention This perfume composition has the following ingredients:
methoxyheptafluoropropane . . . 75%
triethyl citrate . . . 6%
50:50 by weight mixture of diethyl phthalate and silicone DC200 Fluid 1 cs from DOW CORNING . . . 9%
commercially available perfume concentrate . . . 10%

The mixture is produced in a similar manner to Examples 1 and 2, again giving an ethanol-free or alcohol-free perfume composition with a totally clear appearance or the appearance of a perfect solution, the olfactory properties of the perfumes being preserved.

EXAMPLE 4

Ethanol-Free or Alcohol-Free Toilet Water Composition According to the Invention This toilet water composition has the following ingredients:
methoxynonafluorobutane . . . 82%
triethyl citrate . . . 3%
pentacyclomethicone . . . 10%
commercially available perfume concentrate . . . 5%

This composition is prepared by the same mixing procedure as that described in the previous Examples.

EXAMPLE 5

Ethanol-Free or Alcohol-Free Perfume Composition According to the Invention

This perfume composition has the following ingredients, again in percentages by weight:
commercially available perfume concentrate, approx . . . 10
ethoxynonafluorobutane, approx . . . 77
diisopropyl adipate, approx . . . 13

This composition using diisopropyl adipate as an ester co-solvent generally has a less greasy feel than compositions using an association of citrate and silicone, affording the unexpected important technical advantage that the feel of this composition is closer to that of the conventional alcoholic perfume compositions such as toilet waters.

Other modified embodiments of these Examples are well known to those skilled in the art and can include e.g. the incorporation of various other additives normally used in the preparation of perfume compositions such as perfumes or toilet waters, examples being UV filters, antioxidants, colors, etc. Such complementary additives will generally be added in a proportion which can range up to 2% by weight of the final composition.

The invention claimed is:

1. A perfume composition free of ethanol or alcohol, comprising a perfume concentrate comprising at least one essential oil, and a solubilizer comprising an association of a hydrofluoro ether component and of at least one polyacid ester in an amount sufficient to give said composition an essentially clear appearance.

2. The composition of claim 1, wherein the hydrofluoro ether component is selected from the group consisting of methoxynonafluorobutane, ethoxynonafluorobutane, propoxyundecafluoropentane and methoxyheptafluoropropane.

3. The composition of claim 1, wherein the polyacid ester is an ester of a hydroxylated or non-hydroxylated polyacid esterified with a saturated or unsaturated, linear or branched alcohol having between 1 and 30 carbon atoms.

4. The composition of claim 1, wherein the polyacid ester is an ester of a polyacid with an alcohol having between 1 and 12 carbon atoms.

5. The composition of claim 1, wherein the polyacid ester is an ester of a polyacid with an alcohol selected from the group consisting of ethanol, isopropanol and 2-ethylhexanol.

6. The composition of claim 1, wherein the polyacid has between 3 and 10 atoms and comprises a linear or branched, saturated or unsaturated carbon chain optionally substituted by at least one substituent selected from the group consisting of hydroxyl, ketone, and hydroxyl substituted by acetyl.

7. The composition of claim 1, wherein the polyacid is a total ester of a polyacid with a saturated or unsaturated, linear or branched alcohol having between 1 and 30 carbon atoms.

8. The composition of claim 1, wherein the polyacid is a saturated diacid selected from the group consisting of malonic acid, succinic acid, glutaric acid, adipic acid, pimelic acid, suberic acid and azelaic acid; a monounsaturated diacid selected from the group consisting of fumaric acid, maleic acid, citraconic acid, itaconic acid and mesaconic acid; a diunsaturated diacid; muconic acid; a monohydroxylated diacid; tartronic acid; malic acid; citramalic acid; a dihydroxylated diacid; dihydroxymaleic; tartaric acid, a tetrahydroxylated diacid; dihydroxytartaric acid; galactaric acid; glucaric acid; a keto diacid; mesoxalic acid; oxalacetic acid; 2-oxoglutaric acid; 3-oxoglutaric acid, a diketo diacid; 2,3-diketoadipic acid, a saturated triacid; tricarballylic acid; citric acid, an unsaturated triacid; and aconitic acid.

9. The composition of claim 1, wherein the polyacid is citric acid.

10. The composition of claim 1, wherein the polyacid is adipic acid.

11. The composition of claim 1, wherein the polyacid ester is a substantially non-polar ester.

12. The composition of claim 1, wherein the polyacid ester is selected from the group consisting of triethyl citrate, tri(2-ethylhexyl) citrate, diisopropyl adipate and di(2-ethylhexyl) adipate.

13. The composition of claim 1, wherein the polyacid ester represents from 0.1 to 30% by weight of the hydrofluoro ether component.

14. The composition of claim 1, wherein the polyacid ester represents from 1 to 20% by weight of the hydrofluoro ether component.

15. The composition of claim 1, further comprising a silicone selected from a volatile silicone, a dimethicone, a cyclomethicone, pentacyclomethicone, and an organotrisiloxane, the silicone representing from 1 to 20% by weight of the composition.

16. The perfume composition of claim 1, wherein the hydrofluoroether component is present in an amount ranging from about 65 to about 85% by weight, based on the weight of the perfume composition.

17. The composition of claim 16, comprising from about 1 to about 20% by weight of polyacid ester, based on the weight of the perfume composition.

18. The composition of claim 1, comprising from about 5 to about 20% by weight of perfume concentrate.

19. The composition of claim 1, formulated as a body lotion comprising a concentration of perfume concentrate in the order of 5% by weight, based on the weight of the composition.

20. The composition of claim 1, formulated as a perfume, the concentration of perfume concentrate being between 10 and 20% by weight of the perfume composition.

21. The composition of claim 1, wherein the hydrofluoro ether component is a perfluorinated component of the general formula $C_nH_mF_p$—O—$C_xH_yF_z$, in which n is a number ranging from 1 to 12, m is a number ranging from 0 to 25, p is a number ranging from 0 to 11, m+p=2n+1, x is a number from 1 to 12, y is a number from 0 to 25, x is a number from 0 to 11 and y+z=2x+1, and in which m and y may not be equal to 0 simultaneously and p and z may not be equal to 0 simultaneously.

22. The composition of claim 1, comprising an additional component, selected from a second co-solvent, and from a component for improving the properties of the perfume composition.

23. The composition of claim 22, wherein the second co-solvent is a silicone and wherein the component for improving the properties of the perfume composition is promoting the persistence of said composition on the skin, and comprises a phthalate.

24. The composition of claim 23, wherein said phthalate is diethyl phthalate.

25. The composition of claim 1, further comprising up to 2% by weight, based on the composition, of at least one additional additive including a UV filter, an antioxidant or a dye.

26. A method of solubilizing an alcohol-free and ethanol free perfume concentrate comprising admixing the perfume concentrate comprising at least one with a solubilizer comprising an association of comprising a hydrofluoroether component and a polyacid ester, thereby obtaining the perfume composition of claim 1.

27. The method of claim 26, wherein the hydrofluoro ether component is a perfluorinated component of the general formula $C_nH_mF_p$—O—$C_xH_yF_z$, in which n is a number ranging from 1 to 12, m is a number ranging from 0 to 25, p is a number ranging from 0 to 11, m+p=2n+1, x is a number from 1 to 12, y is a number from 0 to 25, x is a number from 0 to 11 and y+z=2x+1, and in which m and y may not be equal to 0 simultaneously and p and z may not be equal to 0 simultaneously.

28. The method of claim 26, further comprising preparing a perfume composition selected from a perfume and a body lotion.

29. An ethanol-free or alcohol-free perfume composition, comprising a perfume concentrate comprising at least one essential oil, and a solubilizer comprising an association of a, hydrofluoro ether component selected from the group consisting of methoxynonafluorobutane, ethoxynonafluorobutane, propoxyundecafluoropentane and methoxyheptafluoropropane, and a polyacid ester selected from the group consisting of triethyl citrate, tri(2-ethylhexyl) citrate, diisopropyl adipate and di(2-ethylhexyl) adipate.

30. The composition of claim 29, further comprising a silicone selected from a volatile silicone, a dimethicone, a cyclomethicone, pentacyclomethicone, and an organotrisiloxane, the silicone representing from 1 to 20% by weight of the composition.

* * * * *